United States Patent
Chen et al.

(10) Patent No.: US 9,499,604 B2
(45) Date of Patent: Nov. 22, 2016

(54) TRAIL MUTANT MEMBRANE-PENETRATING PEPTIDE-ALIKE AND METHODS OF PREPARATION THEREOF

(71) Applicant: CHENGDU HUACHUANG Biotechnology CO., LTD, Chengdu, Sichuan (CN)

(72) Inventors: Shouchun Chen, Sichuan (CN); Juan Yan, Sichuan (CN); Qi Xu, Sichuan (CN); Haiyang Hu, Sichuan (CN); Xianzhou Huang, Sichuan (CN); Lijia Wei, Sichuan (CN)

(73) Assignee: CHENGDU HUACHUANG BIOTECHNOLOGY CO., LTD, Chengdu, Sichuan (CN)

( * ) Notice: Subject to any disclaimer, the term of this patent is extended or adjusted under 35 U.S.C. 154(b) by 0 days.

(21) Appl. No.: 14/764,740

(22) PCT Filed: Oct. 10, 2014

(86) PCT No.: PCT/CN2014/088299
§ 371 (c)(1),
(2) Date: Jul. 30, 2015

(87) PCT Pub. No.: WO2015/103894
PCT Pub. Date: Jul. 16, 2015

(65) Prior Publication Data
US 2016/0145317 A1    May 26, 2016

(30) Foreign Application Priority Data
Oct. 14, 2013   (CN) .......................... 2013 1 0479275

(51) Int. Cl.
C07K 14/705   (2006.01)
C12N 15/10   (2006.01)
A61K 38/00   (2006.01)

(52) U.S. Cl.
CPC ..... *C07K 14/70575* (2013.01); *C12N 15/1037* (2013.01); *A61K 38/00* (2013.01)

(58) Field of Classification Search
CPC .................. C07K 14/70575; C12N 15/1037; A61K 38/00
See application file for complete search history.

*Primary Examiner* — Robert Landsman
(74) *Attorney, Agent, or Firm* — Chung-Ming Shih

(57) ABSTRACT

The invention mainly relates to the field of genetic engineering drugs, in particular to a mutant cDNA sequence obtained by mutating valine at position 114, glutamate at position 116, glycine at position 118, proline at position 119 and glutamine at position 120 in an amino acid sequence at positions 114-281 of an extracellular fragment of a wild-type TRAIL protein respectively into arginines, so as to allow amino acids at positions 114-121 of the TRAIL protein to form a 8-consecutive arginine sequence, and then by gene synthesis and PCR mutation and splicing; and the TRAIL mutant has excellent therapeutic effect for a variety of tumors of different types, and is a new generation of promising drug for highly efficiently inducing tumor cell apoptosis.

9 Claims, 4 Drawing Sheets

TRAIL MUTANT MEMBRANE-PENETRATING PEPTIDE-ALIKE AND METHODS OF PREPARATION THEREOF

FIELD OF THE INVENTION

The invention relates to the field of genetic engineering drugs, in particular to a TRAIL Mutant Membrane-Penetrating Peptide-alike, preparation method and application thereof, and the TRAIL mutant of the invention has excellent therapeutic effect for a variety of tumors of different types, and is a new generation of promising drug for highly efficiently inducing tumor cell apoptosis.

DESCRIPTION OF THE RELATED ART

1. Advance and Significance of Apo 2 L/TRAIL Using in Oncotherapy

Tumor necrosis factor-related apoptosis-inducing ligand (TRAIL) is a member of the tumor necrosis factor (TNF) superfamily, and its gene sequence was obtained by Wiley et al. in 1995 and Pitti et al. in 1996 respectively, and the latter designated it as Apoptin 2 ligand (Apo 2 Ligand, Apo 2 L). Later studies have shown that Apo 2 L and TRAIL are virtually the same protein, therefore customarily the both can be known as Apo 2 L/TRAIL. The function of TRAIL is first to serve as regulator of congenital or acquired immunity of organisms, then to serve as immune surveillance in extrinic apoptosis pathway of cells and exert an anti-neoplastic effect. The greatest advantage of TRAIL is that it can selectively induce apoptosis of a variety of tumor cells and nearly has no toxicity to normal cells. Research data indicated that whether in vitro or in vivo, Apo 2 L/TRAIL has the effect of inducing apoptosis on human tumor cell lines of various origins, including colon (rectal) cancer, lung cancer, breast cancer, prostatic cancer, pancreatic cancer, renal cancer, central nervous system neoplasm, thyroid cancer, lymphoma, leukemia as well as multiple myeloma, etc.

In nearly 20 years since found to today, TRAIL has been developed as an important potential antitumor drug, and clinical trial of TRAIL has entered phase II abroad and entered phase III in China. A large number of experiments in vivo and in vitro have confirmed that TRAIL has tumor specificity and cytotoxicity, and especially when used in combination with a small dose of chemotherapeutic drug, TRAIL shows significant cooperative and synergetic effects. In contrast, it was found by studies that TRAIL resistance resulting from the absence of apoptosis mechanism in organism is definitely associated with rapid growth and transfer of tumor cells.

Tumor is a set of highly heterogeneous diseases, the typing method traditionally in accordance with tissues and organs and pathological changes has been not suitable for diagnosis and treatment of tumors, and the present research direction is towards illustrating gene expression and molecular typing of different tumor cells and giving more targeted treatment to patients. Thorough understanding of antitumor drugs allows people to know that whether cytotoxic drug, molecular targeting drug or monoclonal antibody, the process during which they play a role involves activation of tumor cell apoptosis pathway, and induction of signal pathway of tumor cell apoptosis is the pivot and the central link of these drugs for playing a role, while escaping from apoptosis is an important mechanism of tumor formation and development and drug resistance.

2. Disadvantage of Apo 2 L/TRAIL Used for Tumor Treatment and Countermeasures Recent advances show that treatment of a variety of tumors of different types only dependent on Apo 2 L/TRAIL is still not enough. Though agonistic monoclonal antibody of recombinant human Apo 2 L/TRAIL or TRAIL receptor $DR_4/DR_5$ achieved encouraging results in Phase I clinic treatment, no explicit clinical benefit was shown in subsequent Phase II clinic study. Many studies indicate that normal cells and more than a half (even up to 60%) of passage tumor cell strains show drug resistance to TRAIL. According to overview of Roberta di peitro and Giorgia zauli, Apo 2 L/TRAIL is sensitive to 61 of 92 primary or passage tumor cell strains which have been researched with a sensitive ratio of 66.3%, and resistant to the remaining 31 strains with a drug resistant ratio of 33.7%. Resistance of TRAIL to normal cells is of physiological significance, TRAIL keeps precise regulation in vivo, and only plays a role in eliminating aging and degradation and transferring cells during the growth and development process, but does not kill normal cells. Almost all of TRAIL sensitive tumor cells have similar integrity and function in each link and factor in its apoptosis signal pathway, while each TRAIL resistant tumor cell has defects and variations in some links and factors in apoptosis signal pathway, and these defects and variations cause these drug resistant tumor cells to have apoptotic threshold increased abnormally, more easily escape from apoptotic clearance and thus continuously grow and proliferate.

Many studies show that use of Apo 2 L/TRAIL alone does not produce high-efficiency inhibition and killing effect on many tumor cells. The reason is that the apoptosis signal pathway of tumor cells is a a very complex and huge system, which not only comprises many pro-apoptotic factor, but also comprises a large amount of apoptosis inhibiting factor, and interaction of the both factors determines end results of the tumor cells. Integrity and function of the apoptosis signal pathway are necessary condition for apoptosis of the tumor cells, but not the sufficient condition. Drug, molecular or genetic intervention of multiple different types can enhance sensitivity of TRAIL to tumor cells, and theses drugs comprise different types of chemotherapeutic drugs, natural products, small molecule kinase inhibitors, etc. They enhance TRAIL-induced tumor cell apoptosis activity respectively by strengthening extracellular apoptosis signal pathway (for example upregulating DR expression, enhancing aggregation and redistribution of DR in lipid raft microdomain on the cell membrane, enhancing endocytosis of TRAIL/DR complex in the cell membrane, promoting recruitment of DISC to the TRAIL/DR complex, activating activity of Caspase (Caspase 8) of initial phase, inhibiting activities of apoptosis antagonizing factors FLIP, XIAP and IAP, etc.) or mitochondrial apoptosis signal pathway (for example enhancing depolarization of mitochondrial membrane potential, promoting increase of mitochondrial permeability and releasing Cyt c, Smac or ART, promoting Bid to be cleaved into tBid, promoting oligomerization of Bax and Bad, and inhibiting apoptosis antagonizing factors Bcl-2, Bcl-xL, Bcl-w, Mcl-1 and survivin) or inhibiting other cell survival signal pathways (such as ERK/PI3K/AKt, MEK, Jak-STAT 3, MAPK and NF-κB) or a combination of several pathways.

Despite development of TRAIL and agonistic monoclonal antibody of TRAIL receptor thereof is obstructed temporarily, as the signal pathway of cell apoptosis is elucidated fully, and the conversion relation between apoptosis/resistance is disclosed fully, development of targeting antitumor drugs based on the apoptosis signal pathway is not be stopped. At present, the studies are focused on application of TRAIL in combination with cytotoxic drugs, but most of the experiments show that this combination could only produce significant cooperative and synergetic effect on tumor cells relatively sensitive to TRAIL, but could not completely reverse drug resistance produced by a variety of different drug resistant mechanisms. Because TRAIL and cytotoxic drugs belong to two classes of different drugs, there are discrepance and difference between drug varieties and doses, administration routes and modes of action, it is less likely to develop a single, stable and controllable new drug, and after the TRAIL is used in combination with the cytotoxic drugs, its toxic and side effects still exist, thus advantage is not obvious.

3. Design Ideas of TRAIL Mutant Membrane-Penetrating Peptide-Alike

Apoptosis proteins finally exert effect in a core position in the cell membrane, and the cell membrane is a biological barrier for transferring therapeutic bioactive substance into the cell. Due to hydrophilicity of Apoptosis proteins, bioactive molecules can not penetrate the cell membrane freely, resulting in limitations on its effects and practical application. The cell-penetrating peptide is a type of positively charged cationic short peptide which has ability to penetrate the cell membrane and mostly has 20-30 amino acids in length, is a novel drug transport and delivery technique developed in recent decades and is also known as protein transduction domain (PTD).

In 1988, Green and Frankel first demonstrated that trans-activating protein TAT of human immunodeficiency virus (HIV-1) can be transferred into cytoplasm and nucleus across the membrane. One of arginine-rich TAT polypeptides as shown in SEQ ID NO: 6 (GRKKRRQRRRGY) has ability to penetrate the membrane and transduct the protein, and can mediate a variety of substances of multiple origins, such as gene, protein, polypeptide and chemically synthesized nano-particles to enter the cell membrane and even the nucleus. Later, it was successively found that *drosophila* homeobox transcription factor ANTP, herpes simplex virus type I (HSV-1) transcription factor VP22, Transpotan, polyarginine and other sequences has ability to penetrate the cell membrane, and now hundreds of peptide fragments with cell-penetrating function have been found.

According to different standards, cell-penetrating peptides can be classified into different categories. In view of structural characteristics, in early days the cell-penetrating peptides were simply classified into: (1) the cell-penetrating peptide without a typical structure and with a large number of cations, such as TAT and penetratin; and (2) the amphiphilic α helical peptide derived from a protein signal sequence. In view of origins, the cell-penetrating peptides were classified into two naturally-occurring and artificially synthesized categories, and can be further classified into three categories: (1) the cell-penetrating peptides derived from protein, such as penetratin, TAT and pVEC, which generally have the smallest effective fragment of transporter, i.e. protein transduction portion and membrane translocation sequence; (2) the model cell-penetrating peptides, such as MAP and Arg(7), which are artificially synthesized in order to form a determined amphiphilic a helix or simulate a known cell-penetrating peptide structure, wherein the polyarginine and polylysine synthesized according to the cell-penetrating peptide structure has cell-penetrating ability higher than transduction activity of the TAT protein; and (3) the cell-penetrating peptides which are artificially designed and synthesized, such as PEP-1, MPG and Transportan, which are generally chimeric polypeptides, comprising one hydrophobic portion and one hydrophilic portion, for example PEP-1 as shown in SEQ ID NO: 7 (KETWW ETWWT EWSQP KKKRK V) comprising one fragment rich in hydrophobic tryptophan motifs (KETWW ETWWT EW), one spacer (SQP) and one region rich in hydrophilic lysine motifs (KKKRKV). Such a peptide fragment has more advantages that PEP-1 does not have to be covalently linked with target macromolecules and can effectively transduce a protein of natural conformation into the cell by directly mixing with macromolecules.

The key structural of the amino acids with cell-penetrating function is that its main molecular composition is rich in alkaline amino acids, such as arginine, lysine and histidine. The alkaline amino acids are important features of composition of cell-penetrating proteins of this type. These amino acids bear strong positive charges, and may interact with cell membrane lipid molecules with negative charges to mediate the cell-penetrating process, wherein arginine residues play an important role in cellular internalization of proteins. At present, there are two views in the action mechanism related to polyarginine-transduced protein endocytosis: first, protein is directly transduced into the cell through pores temporarily formed by arginine in the cell membrane and the lipid bilayer; second, protein is transduced into the cell through multiple forms of mediated endocytosis, including macropinocytosis, caveolin-medicated type, clathrin-medicated type, phagocytosis as well as endosome communication and other mechanisms. TRAIL induces aggregation and redistribution of death receptors in lipid raft microdomain on the tumor cell membrane, recruits Fas-Associated death domains (FADD) and Caspase-8 with or without endocytosis of TRAIL-DR4/5 complex to assemble death inducing signaling complex (DISC) and initiates a waterfall cascade process of apoptotic effects by cleaving Caspase-8. Most of literatures believe that internalization of the TRAIL-DR4/5 complex is necessary for continuous amplification of apoptotic signal. Traditionally foreign protein is expressed in fusion with the cell-penetrating protein, and the expressed protein may have changed spatial conformation of the protein molecule so as to lose its biological activity. Furthermore, fusion protein increases antigenicity of original protein molecule so as to create security risks.

We allow the TRAIL protein to form a similar cell-penetrating peptide-like amino acid sequence, namely perform cell-penetrating peptide-like mutation on wide-type TRAIL protein (1-281aa) by selectively mutating several amino acids at N-terminal of the amino acid sequence encoding a soluble fragment (114-281aa) of the TRAIL protein, and now more than 10 different cell-penetrating peptide-like mutants have been obtained. The invention breaks the design ideas of original cell-penetrating peptide fusion protein, selectively mutates valine at position 114, glutamate at position 116, glycine at position 118, proline at position 119 and glutamine at position 120 at N-terminal of the amino acid sequence at positions 114-281 of an extracellular fragment of a TRAIL wild-type protein respectively into arginines, so as to allow amino acids at positions 114-121 of the TRAIL protein to form a 8-consecutive arginine sequence. Endogenous 8-consecutive arginine sequence results in the smallest change in N-terminal amino acid sequence of the extracellular segment of TRAIL (the sequence of arginines at position 115, position 117 and position 121 is reserved), thus maintaining spatial conformation and biological activity of the TRAIL protein to a greatest extent, and also constructing a 8-consecutive arginine sequence with cell-penetrating function, and we named the TRAIL Mutant Membrane-Penetrating Peptide-alike of the invention as TRAIL-Mu3. TRAIL Mutant Membrane-Penetrating Peptide-alike is a new design idea of a cell-penetrating peptide fusion protein.

SUMMARY OF THE INVENTION

Aiming at the disadvantages of the prior art, an objective of the invention is to provide a novel TRAIL Mutant Membrane-Penetrating Peptide-alike which can substantially enhance antitumor activity of TRAIL wild-type protein, and can especially reverse drug resistance produced by a variety of drug resistant tumors to TRAIL wild-type protein. The prepared mutant protein can directly enter cytoplasm by penetrating the cell membrane to exert effect rapidly, and can promote aggregation and internalization of death receptor/mutant protein complexes in lipid raft microdomain on the cell membrane, to enchance transduction of exogenous apoptotic signal pathway. TRAIL Mutant Membrane-Penetrating Peptide-alike has excellent therapeutic effect for a variety of tumors of different types, and is a new generation of promising drug for highly efficiently inducing tumor cell apoptosis.

In order to achieve the above objective, the invention employs the technical solution as follows: A TRAIL Mutant Membrane-Penetrating Peptide-alike, wherein the mutant is a protein comprising a cell-penetrating peptide-like structure formed by selectively changing an amino acid coding sequence at positions 114-121 of an extracellular fragment of a TRAIL wild-type protein as shown in SEQ ID NO: 5 to TRAIL mutant-type protein as shown in SEQ ID NO: 2, namely mutating valine at position 114 into arginine, glutamate at position 116 into arginine, glycine at position 118 into arginine, proline at position 119 into arginine and glutamine at position 120 into arginine, so as to allow N-terminal of the mutant protein to form a 8-consecutive arginine coding sequence.

Further, the cDNA sequence encoding the said mutant is as SEQ ID NO: 1.

A second objective of the invention is to provide a preparation method of a TRAIL Mutant Membrane-Penetrating Peptide-alike, comprising the steps as follows:

A) amplifying and cloning a cDNA fragment;
B) constructing and identifying an expression vector;
C) fusing and expressing a recombinant TRAIL protein;
D) purifying the TRAIL protein; and
E) identifying the TRAIL protein.

Further, in step B, the step of constructing and identifying the said expression vector comprises:

$B_1$) excising a corresponding fusion tag sequence in a prokaryotic expression vector; and $B_2$) cloning an optimized cDNA sequence encoding the TRAIL Mutant Membrane-Penetrating Peptide-alike protein into the prokaryotic expression vector to achieve high-efficiency soluble non-fusion expression.

Further, in step $B_1$, the said prokaryotic expression vector is pET 32a or pTWIN 1.

Further, in step C, when the said recombinant protein is expressed, the induction temperature is 18-24° C.

Further, in step D, the step of purifying the said TRAIL protein comprises:

$D_1$) using cation exchange resin in the first step for purification to capture target protein in supernatant after bacteria disruption;

$D_2$) using hydroxyapatite resin in the second step for moderate purification to further improve purity of the protein and remove endotoxin; and $D_3$) using anion exchange resin in the final step for fine purification to make the product to meet requirements for industrialized enlargement and future clinic application.

A third objective of the invention is to provide application of a TRAIL Mutant Membrane-Penetrating Peptide-alike in antitumor drugs.

The action mechanism of the invention for inducing tumor cell apoptosis is that the TRAIL Mutant Membrane-Penetrating Peptide-alike can rapidly enter the tumor cell by cell penetrating and exert effect of inducing cell apoptosis. Furthermore, the TRAIL Mutant Membrane-Penetrating Peptide-alike can also effectively promote aggregation and redistribution of death receptors in lipid raft microdomain on the cell membrane and/or internalization of TRAIL-DR4/DR5 complex, and enhance transduction of exogenous apoptotic signal pathway.

The beneficial technical effects of the invention include that:

1. A new protein structure employs a minimum of mutation sites, has minimal influence on the protein structure but obtains the greatest function. The TRAIL Mutant Membrane-Penetrating Peptide-alike only has mutations of five nonconsecutive sites, because mutations of the sites occur at the amino terminal of the protein, there is less influence on biological activity and stability of the protein, but cell-penetrating ability over the cell-penetrating peptide fusion protein is obtained;

2. There is a high protein expression and high soluble expression ratio, a modified form of a high-efficiency prokaryotic expression vector pET32a or pTWIN 1 is employed, the expression vector can achieve a higher expression level and a higher soluble expression ratio than the TRAIL wild-type protein in a wider range of induction temperature from 18 to 24° C., and the soluble protein expression ratio is up to 80%-100%;

3. Unlike the purification and preparation process of the TRAIL wild-type protein, the process of the invention significantly improves effectiveness, recovery rate and product quality, accordingly reduces purification cost without effective affinity chromatography purification method, has significant enlargement potential and can fully meet the future clinic requirements; and 4. The TRAIL Mutant Membrane-Penetrating Peptide-alike has a wide range of biological activity in vitro compared to the TRAIL wild-type protein, has antitumor activity significantly improved in almost all types of tumor cells which have been detected, especially for tumor cell strains resistant to the TRAIL wild-type protein, can markedly reverse resistance of these cells to the TRAIL wild-type protein and has greater therapeutic effect.

BRIEF DESCRIPTION OF THE DRAWINGS

In order to illustrate embodiments of the invention or the technical solution in the prior art more clearly, the drawings required to be used in description of the embodiments or the prior art will be briefly introduced below, obviously, the drawings in the description below are only some embodiments of the invention, and for those ordinary skilled in the art, other drawings will be obtained according to these drawings without creative work.

DETAILED DESCRIPTION OF THE PREFERRED EMBODIMENT

Figure 1:
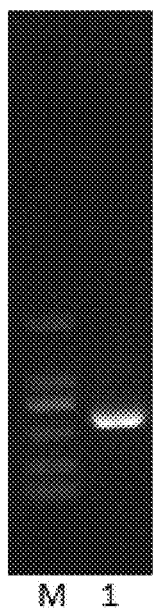
FIG. 1: electrophoretogram of PCR product of TRAIL-Mu3 fragment; electrophoresis condition: 3% Agarose, voltage 100V, 20 min; Lane 1: electrophoresis bands of PCR product of TRAIL-Mu3 fragment; M: DL2000 (molecular weights of bands from top to bottom: 2000 bp, 1000 bp, 750 bp, 500 bp, 250 bp and 100 bp), loading amount being 5 μl, and loading amount of PCR product being 5 μl.

The technical solution in the embodiments of the invention will be described clearly and fully below in conjunction with the drawings in the embodiments of the invention, and obviously, the described embodiments are only a part of the invention. Based on the embodiments in the invention, all other embodiments obtained by those ordinary skilled in the art without any further creative work shall fall within the scope claimed by the invention.

Embodiment 1

Sequence and Primer Design of TRAIL Mutant Membrane-Penetrating Peptide-Alike

A protein comprising a cell-penetrating peptide-like structure is formed by selectively changing an amino acid coding sequence at positions 114-121 of an extracellular fragment of a TRAIL wild-type protein as shown in SEQ ID NO: 5 to TRAIL mutant-type protein as shown in SEQ ID NO: 2, namely mutating valine at position 114 into arginine, glutamate at position 116 into arginine, glycine at position 118 into arginine, proline at position 119 into arginine and glutamine at position 120 into arginine with 5 mutation sites, so as to allow N-terminal of the mutant protein to form a 8-consecutive arginine coding sequence.

A cDNA sequence encoding the mutant is as SEQ ID NO: 1, and an amino acid sequence of the mutant is as SEQ ID NO: 2.

Primer is synthesized as follows:

upstream primer Mu3-TR-NdeI is as set forth in SEQ ID NO: 3; and downstream primer TR-Eco-R is as set forth in SEQ ID NO: 4.

Embodiment 2

A TRAIL-Mu3 fragment is amplified by PCR and ligated to a T vector, and individual colonies of the ligated product are picked and identified.

A TRAIL-Mu3 fragment is mutated and amplified by PCR using pMD19/TRAIL plasmid as a template, and ligated to a T vector, and individual colonies of the ligated product are picked and identified. For primer design, see Embodiment 1, and the pMD19/TRAIL plasmid is prepared in laboratory.

Experimental Procedures

I. PCR Amplification of Target Fragment of TRAIL-Mu3

1. Amplify the target fragment of TRAIL-Mu3 by using pMD19/TRAIL as a template and a pair of Mu3-TR-NdeI/TR-Eco-R primer, and formulate a reaction system according to Table 1, which is 50 µl.

TABLE 1

TRAIL-Mu3 PCR Reaction System (50 µl)

| Reagents | Reaction system |
| --- | --- |
| Purified pMD19/TRAIL plasmid | 1 µl |
| 10x Ex Taq Buffer (Mg$^{2+}$ free) | 5 µl |
| dNTP Mix (2.5 mM each) | 4 µl |
| 25 mM MgCl$_2$ | 3 µl |
| TaKaRa Ex Taq | 1 µl |
| Primer Mu3-TR-NdeI (10 pmol/µl) | 1 µl |
| Primer TR-Eco-R (10 pmol/µl) | 1 µl |
| RNase-Free Water | 34 µl |

2. Homogeneously mix by vortex and shaking, briefly centrifuge, and collect the solution at the bottom of a tube.

3. For PCR amplification condition, see Table 2.

TABLE 2

TRAIL-Mu3 PCR Reaction Condition

| Steps | Temperature | Time | |
| --- | --- | --- | --- |
| Pre-denaturation | 94° C. | 1 min | |
| Denaturation | 94° C. | 30 s | |
| Annealing | 58° C. | 30 s | 25 cycles |
| Extension | 72° C. | 45 s | |
| Final extension | 72° C. | 3 min | |

4. Perform electrophoresis and photography.

5. Gel extract the target fragment of TRAIL-Mu3 amplified by PCR by using Omega gel extraction kit, elute with 50 µl of ultrapure water, and perform electrophoresis and photography for use.

II. Ligation of Gel-Extracted Target Fragment to pMD19 T Vector

1. Ligate the gel-extracted target fragment using TaKaRa pMD19-T Vector kit, and for a ligation system, see Table 3.

TABLE 3

Reaction System for Ligation of TRAIL-Mu3 to pMD19 T (10 µl)

| Reagent | Reaction system |
| --- | --- |
| pMD19 T vector | 1 µl |
| Target fragment (TRAIL-Mu3) | 4 µl |
| Ligase (sol I) | 5 µl |

2. Incubate in a metal bath at 16□ overnight.

3. Add 10 µl of ligated product to 100 µl of Top10 competent cells, and place into an ice bath for 30 min.

4. Heat shock in a water bath at 42° C. for 90s.

5. Incubate on ice for 2 min.

6. Add 500 µl of SOC culture medium, and culture at 37° C. with shaking for 45 min.

7. After centrifuging transformed competent cells, discard 400 µl of culture medium on a super clean bench, remain about 100 µl of culture medium, blow bacteria evenly, spread all bacteria on LB solid medium containing Amp, and culture at 37° C. overnight.

III. Picking of Individual Colonies and Identification by Enzyme Digestion (I) Picking of Individual Colonies 1. Prepare multiple sterilized test tubes, and add 100 ml of ampicillin LB liquid medium to the test tubes.

2. Separate the medium into respective test tubes, with each tube containing about 4 ml.

3. On a plate where colonies have grown, clamp a pipette tip using fully burnt forceps to pick up the colonies grown on the plate, pick up 7 pMD19/TRAIL-Mu3 colonies and put the pipette tip into the test tube containing LB liquid medium.

4. Tie respective test tubes up, place into a shaker clamp for fully fixation, and shake at 37° C. and 220 rpm overnight.

(II) Plasmid Extraction

1. Add 1 ml of each bacterial solution to a centrifuge tube respectively, centrifuge at 10000 g for 1 min, and draw the supernatant as much as possible.

2. Add 250 µl of Solution I (with RNAase A added in advance) to the centrifuge tube with remaining bacterial precipitate, to thoroughly suspend the bacterial precipitate.

3. Add 250 µl of Solution II, gently mix to adequately cleave the bacteria, where the bacterial solution become clear and sticky, and finish this step within 5 min.

4. Add 350 µl of Solution III to the centrifuge tube, mix upsidedown at once where white flocculent precipitate appears, and centrifuge at 13000 g for 10 min where precipitate is formed at the bottom of the centrifuge tube.

5. Respectively add the supernatant obtained in step 4 to 2 HiBind Miniprep adsorption columns which have been enclosed in a collecting tube, be careful not to precipitate out, centrifuge at 10000 g for 1 min, discard the waste solution in the collecting tube, and put the adsorption columns back into the collecting tube.

6. Add 500 µl of Buffer HB to the collecting tube, centrifuge at 10000 g for 1 min, discard the waste solution in the collecting tube, and put the adsorption columns back into the collecting tube.

7. Add 700 µl of Wash Buffer to the collecting tube, centrifuge at 10000 g for 1 min, discard the waste solution in the collecting tube, and put the adsorption columns back into the collecting tube.

8. Repeat step 7.

9. Put the adsorption columns back into the collecting tube, centrifuge at 13000 g for 2 min, and discard the waste solution in the collecting tube.

10. Place each adsorption column into a new 1.5 ml Ep tube, add 65 μl of Elution Buffer dropwise overhead the middle of each adsorption film, stand at room temperature for several minutes, centrifuge over 13000 g for 1 min, and collect the plasmid solution to a 1.5 ml Ep tube.

11. Obtain 60 μl of plasmid DNA respectively, and preserve the plasmid at −20° C.

(III) Identification by Enzyme Digestion

1. Double digest pMD19/TRAIL-Mu3 plasmid with EcoR I and Hind III. For reaction system for enzyme digestion, see Table 4.

TABLE 4

Reaction System for pMD19/TRAIL-Mu3 Enzyme Digestion (10 μl)

| Reagents | Volume |
|---|---|
| pMD19/TRAIL-Mu3 DNA | 5 μl |
| EcoR I | 0.5 μl |
| Hind III | 0.5 μl |
| 10x M Buffer | 1 μl |
| dH$_2$O | 3 μl |

2. Put Ep tubes into a multi-purpose incubator, and incubate at 37° C. for 2 h.

3. Identify by electrophoresis after finishing enzyme digestion.

(IV) Select Strains which are Properly Digested and Succeed in Ligation, Preserve Glycerol Strains, Send for Sequencing and Preserve the Strains Sequenced Properly.

Experimental Results

I. Results of PCR Amplification of Target Fragment

The target fragment of TRAIL-Mu3 was amplified by using a pair of Mu3-TR-NdeI/TR-Eco-R primers, the fragment has molecular weight of around 500 bp, and as shown in FIG. 1, the target gene was obtained according to the PCR reaction condition described above.

II. Results of Ligation to pMD19 T Vector and Transformation

1. There were colonies grown on the plate, but the density was not high.

2. Individual colonies were picked up, there were bacteria grown in some test tubes on the second day, and the density was normal.

Figure 2:
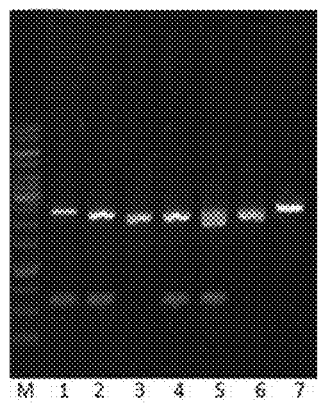
FIG. 2: electrophoretogram of pMD19/TRAIL-Mu3 identified by enzyme digestion; electrophoresis condition: 1% Agarose, voltage 150V, 30 min; Lanes 1-7: electrophoretogram of plasmid extracted from pMD19/TRAIL-Mu3 strain after enzyme digestion; M: GeneRuler1 kb DNA Ladder (molecular weights of bands from top to bottom: 10000 bp, 8000 bp, 6000 bp, 5000 bp, 4000 bp, 3500 bp, 3000 bp, 2500 bp, 2000 bp, 1500 bp, 1000 bp, 750 bp, 500 bp and 250 bp), loading amounts of identified products being 10 μl, and loading amount of Marker being 4l1.

3. The plasmid was identified by an enzyme digestion method, the pMD19/TRAIL-Mu3 plasmid can be identified by double enzyme digestion with EcoR I and Hind III, and the plasmid succeeding in ligation should give a vector fragment of around 2.7 Kb and a target fragment of around 500 bp after enzyme digestion. As shown in FIG. 2, 4 samples such as pMD19/TRAIL-Mu3 4$^{\#}$, 5$^{\#}$, 6$^{\#}$ and 8$^{\#}$ are positive clones. The positive clones were sent to Beijing Genomics Institute for sequencing, and strains with plasmids having completely correct sequence and containing TRAIL-Mu3 target gene sequence are obtained.

Embodiment 3

A TRAIL-Mu3 target fragment is ligated to pET32a or pTWIN1 respectively, and individual colonies of the ligated product are picked and identified.

The TRAIL-Mu3 target fragment and the vector pET32a or pTWIN1 are respectively double digested with Nde I and EcoR I. The TRAIL-Mu3 fragment is ligated to the vector pET32a with Trx fusion tag sequence excised or the vector pTWIN1 with Intein sequence excised, and transformed into a Top10 competent cell, and individual colonies are picked up and identified by double enzyme digestion with Xba I and EcoR I. The TRAIL-Mu3 target fragment is from Embodiment 2, and the vector pET32a or pTWIN1 is prepared in laboratory.

Experimental Procedures

I. Ligation of the Target Fragment TRAIL-Mu3 to pET32a or pTWIN1 Plasmid after Double Enzyme Digestion 1. Double digest the vector and the target gene fragment with NdeI and EcoRI, see Table 5 for the enzyme digestion system, wherein the reaction system is 100 μl.

TABLE 5

Reaction System for Double Enzyme Digestion of TRAIL-Mu3 and pET32a or pTWIN1 (100 μl)

| Reagents | Volume | |
|---|---|---|
| DNA designation | pET32a or pTWIN1 plasmid | TRAIL-Mu3 DNA |
| DNA | 50 μl | 45 μl |
| Nde I | 5 μl | 3 μl |
| EcoR I | 5 μl | 3 μl |
| 10x H Buffer | 10 μl | 10 μl |
| dH2O | 30 μl | 39 μl |

2. Put Ep tubes into a multi-purpose incubator, and incubate at 30° C. for 2 h.

3. Perform gel extraction by using OMEGA gel extraction kit, and elute the vector and the target fragment respectively with 30 μl of ultrapure water. Perform electrophoresis and photography.

4. Ligate the gel-extracted target fragment and vector, and for a ligation system, see Table 6.

TABLE 6

Reaction System for Ligation of TRAIL-Mu3 to pET32a or pTWIN1 (10 μl)

| Reagents | Reaction system | Reaction System |
|---|---|---|
| Vector (pET32a) | 1 μl | — |
| Vector (pTWIN1) | — | 1 μl |
| TRAIL-Mu3 | 4 μl | 4 μl |
| ligase (sol I) | 5 μl | 5 μl |

5. Incubate in a metal bath at 16° C. overnight.

6. Add 10 μl of ligated product to 100 μl of Top10 competent cells, and place into an ice bath for 30 min.

7. Heat shock in a water bath at 42° C. for 90 s.

8. Incubate on ice for 2 min.

9. Add 500 μl of SOC culture medium, and culture at 37° C. with shaking for 45 min.

10. After centrifuging transformed competent cells, discard 400 μl of culture medium on a super clean bench, and remain about 100 μl of culture medium.

11. Blow bacteria evenly, spread all bacteria on LB solid medium containing Amp, and culture at 37° C. overnight.

II. Picking of Individual Colonies and Identification by Enzyme Digestion (I) Picking of Individual Colonies 1. Prepare multiple sterilized test tubes, and add 100 ml of ampicillin LB liquid medium to each tube.

2. Separate the medium into respective test tubes, with each tube containing about 4 ml.

3. On a plate where colonies have grown, clamp a pipette tip using fully burnt forceps to pick up the colonies grown on the plate, and pick up 8 colonies from the pET32a/TRAIL-Mu3 plate or 5 colonies from the pTWIN1/TRAIL-Mu3 plate. Put the pipette tip into the test tube containing LB liquid medium.

4. Tie respective test tubes up, place into a shaker clamp for fully fixation, and shake at 37° C. and 220 rpm overnight.

(II) Plasmid Extraction

1. Add 1 ml of each bacterial solution to a centrifuge tube respectively. Centrifuge at 10000 g for 1 min, and draw the supernatant as much as possible.

2. Add 250 μl of Solution I (with RNAase A added in advance) to the centrifuge tube with remaining bacterial precipitate, to thoroughly suspend the bacterial precipitate.

3. Add 250 μl of Solution II, gently mix to adequately cleave the bacteria, where the bacterial solution become clear and sticky, and finish this step within 5 min.

4. Add 350 μl of Solution III to the centrifuge tube, mix upsidedown at once where white flocculent precipitate appears, and centrifuge at 13000 g for 10 min where precipitate is formed at the bottom of the centrifuge tube.

5. Respectively add the supernatant obtained in step 4 to 2 HiBind Miniprep adsorption columns which have been enclosed in a collecting tube, be careful not to precipitate out, centrifuge at 10000 g for 1 min, discard the waste solution in the collecting tube, and put the adsorption columns back into the collecting tube.

6. Add 500 μl of Buffer HB to the collecting tube, centrifuge at 10000 g for 1 min, discard the waste solution in the collecting tube, and put the adsorption columns back into the collecting tube.

7. Add 700 μl of Wash Buffer to the collecting tube, centrifuge at 10000 g for 1 min, discard the waste solution in the collecting tube, and put the adsorption columns back into the collecting tube.

8. Repeat step 7.

9. Put the adsorption columns back into the collecting tube, centrifuge at 13000 g for 2 min, and discard the waste solution in the collecting tube.

10. Place each adsorption column into a new 1.5 ml Ep tube, add 65 μl of Elution Buffer dropwise overhead the middle of each adsorption film, stand at room temperature for several minutes, centrifuge over 13000 g for 1 min, and collect the plasmid solution to a 1.5 ml Ep tube.

11. Obtain 60 μl of plasmid DNA respectively. Preserve the plasmid at −20° C.

(III) Identification by Enzyme Digestion

1. Double digest pET32a/TRAIL-Mu3 or pTWIN1/TRAIL-Mu3 plasmid with Xba I and EcoR I. For reaction system for enzyme digestion, see Table 7.

TABLE 7

Reaction System for enzyme digestion of pET32a/TRAIL-Mu3 or pTWIN1/TRAIL-Mu3 (10 μl)

| Reagents | Volume | |
|---|---|---|
| pET32a/TRAIL-Mu3 plasmid | 5 μl | — |
| pTWIN1/TRAIL-Mu3 plasmid | — | 5 μl |
| Xba I | 0.5 μl | 0.5 μl |
| EcoR I | 0.5 μl | 0.5 μl |
| 10x M Buffer | 1 μl | 1 μl |
| dH2O | 3 μl | 3 μl |

2. Put Ep tubes into a multi-purpose incubator, and incubate at 37° C. for 2 h.

3. Identify by electrophoresis after finishing enzyme digestion.

(IV) Select Strains which are Properly Digested and Succeed in Ligation, Preserve Glycerol Strains, and Send for Sequencing.

Experimental Results

Figure 3:
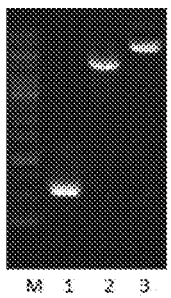
FIG. 3: electrophoretogram of TRAIL-Mu3 and plasmids of pET32a and pTWIN1 after Nde I and EcoR I enzyme digestion; electrophoresis condition: 1% Agarose, voltage 150V, 25 min; Lane 1: electrophoresis band of TRAIL-Mu3 for gel extraction after enzyme digestion; Lane 2: electrophoresis band of pET32a for gel extraction after enzyme digestion; Lane 3: electrophoresis band of pTWIN1 for gel extraction after enzyme digestion; M: GeneRuler1 kb DNA Ladder (molecular weights of bands from top to bottom: 10000 bp, 8000 bp, 6000 bp, 5000 bp, 4000 bp, 3500 bp, 3000 bp, 2500 bp, 2000 bp, 1500 bp, 1000 bp, 750 bp, 500 bp and 250 bp), loading amounts being 5 μl; and loading amount of PCR product being 3 μl.

I. Theoretically, target fragments of about 500 bp, 5.4 kb and 6.6 kb will be obtained after double enzyme digestion of TRAIL-Mu3, pET32a and pTWIN1 with Nde I and Eco RI, and as shown in FIG. 3, single bands expected were obtained by gel extraction after enzyme digestion.

II. Results of ligation of TRAIL-Mu3 target fragments respectively to pET32a or pTWIN1 and transformation 1. There were colonies grown on the plate, and the density was normal.

2. Individual colonies were picked up, there were bacteria grown in some test tubes on the second day, and the density was normal.

Figure 4:
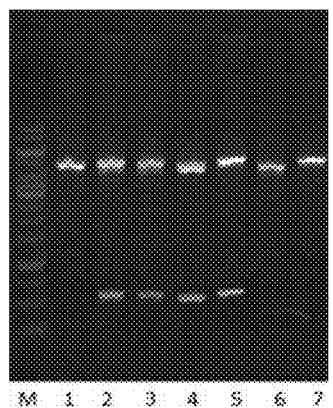
FIG. 4: electrophoretogram of plasmids of pET32a/TRAIL-Mu3 identified by enzyme Xba I and EcoR I digestion; electrophoresis condition: 1% Agarose, voltage 150V, 30 min; Lanes 1-7: electrophoretogram of plasmids extracted from pET32a/TRAIL-Mu3 strain after enzyme digestion; M: GeneRuler1 kb DNA Ladder (molecular weights of bands from top to bottom: 10000 bp, 8000 bp, 6000 bp, 5000 bp, 4000 bp, 3500 bp, 3000 bp, 2500 bp, 2000 bp, 1500 bp, 1000 bp, 750 bp, 500 bp and 250 bp); loading amounts of identified products being 10 μl, and loading amount of Marker being 5 μl.
Figure 5:
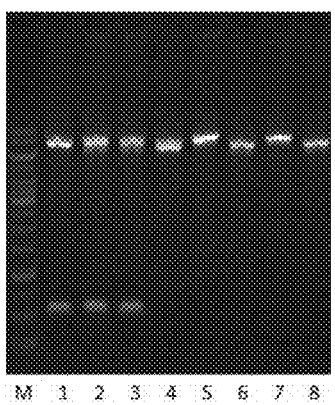
FIG. 5: electrophoretogram of plasmids of pTWIN1/TRAIL-Mu3 identified by enzyme Xba I and EcoR I digestion; electrophoresis condition: 1% Agarose, voltage 150V, 30 min; Lanes 1-8: electrophoretogram of plasmids extracted from pTWIN1/TRAIL-Mu3 strain after enzyme digestion; M: GeneRuler1 kb DNA Ladder (molecular weights of bands from top to bottom: 10000 bp, 8000 bp, 6000 bp, 5000 bp, 4000 bp, 3500 bp, 3000 bp, 2500 bp, 2000 bp, 1500 bp, 1000 bp, 750 bp, 500 bp and 250 bp); loading amounts of identified products being 10 μl, and loading amount of Marker being 5 μl.

3. The plasmid was identified by an enzyme digestion method, the pET32a/TRAIL-Mu3 or pTWIN1/TRAIL-Mu3 plasmid can be identified by double enzyme digestion with Xba I and EcoR I, and the plasmid succeeding in ligation should give vector fragments of around 5.4 Kb and 6.6 Kb and a target fragment of around 550 bp after enzyme digestion. As shown in FIG. 5, 3 samples of pTWIN1/TRAIL-Mu3 are positive clones; and as shown in FIG. 4, 4 samples of pET32a/TRAIL-Mu3 are positive, and the positive plasmids were sent to Beijing Genomics Institute for sequencing, and plasmids sequenced to be correct were preserved.

Embodiment 4

Expression test on pTWIN1/TRAIL-Mu3 or pET32a/TRAIL-Mu3 is performed.

Competent *Escherichia Coli* BL21 (DE3) is transformed with plasmids sequenced to be correct that is obtained in Embodiment 3, and one individual colony is picked up respectively for examining expression effects.

Experimental Procedures

I. Plasmid Transformation and Strain Preservation

1. Formulate 100 ml of LB culture medium, and sterilize at 121° C. for 20 min.

2. Add 1 μl of pTWIN1/TRAIL-Mu3 or pET32a/TRAIL-Mu3 plasmid each to BL21 (DE3) competent cell, and place in an ice bath for 30 min.

3. Heat shock in a water bath at 42° C. for 90 s.

4. Incubate on ice for 3 min.

5. Spread all 20 μl of transformed competent cells on LB solid medium containing Amp, and culture at 37° C. overnight.

6. Pick up one individual colony from a plate after colonies were grown on the plate on the second day, add to 50 ml LB (Amp$^+$), and culture at 37° C. overnight.

7. Preserve 20 tubes of glycerol strains, with a final glycerol concentration of 15% at −20° C.

II. Expression of Strains

1. Add 1000 μl of culture solution of pTWIN1/TRAIL-Mu3 or pET32a/TRAIL-Mu3 cultured overnight to 50 ml LB (Amp$^+$) medium. After inoculation, culture at 37° C. with shaking at 250 rpm for 3 h, and then reduce the culture temperature to 24° C. Add 0.1M IPTG at a ratio of 1% for inducing culture, take 0.5 ml of the sample for centrifugation before induction and discard supernatant, add 50 μl H$_2$O for resuspension and then add 50 µl 2× loading buffer to prepare an induced electrophoresis sample.

2. Harvest bacteria after induction overnight, detect $A_{600}$ value, take 150 µl of the sample for centrifugation and discard supernatant, add 50 µl $H_2O$ for resuspension and then add 50 µl 2× loading buffer to prepare an induced electrophoresis sample, and centrifuge the remaining bacterial solution with a 5430R Model centrifuge at 12000 rpm for 5 min.

3. Take 50 ml of the culture solution for centrifugation to obtain bacteria, resuspend with 8 ml of 50 mM $Na_2HPO_4$, and disrupt bacteria by ultrasonic waves. Bacteria disruption condition: disrupting bacteria with Φ6 probe, 200 W pulse for 2 s, then pausing for 2 s, and cycling for 10 min in total.

4. Centrifuge 1 ml of the disrupted bacterial solution at 12000 rpm for 10 min, separate the supernatant from the precipitate, resuspend the precipitate with 1 ml $H_2O$, and add 20 µl of each supernatant and precipitate resuspension solution to 30 µl $H_2O$ and 50 µl 2× loading buffer to prepare electrophoresis samples.

5. Place the prepared electrophoresis samples in a boiling water bath for treatment for 10 min, centrifuge by using a 5430R Model centrifuge and A-45-30-11 Model rotor at 12000 rpm for 10 min, and take 10 µl of each supernatant for electrophoresis.

Experimental Results

Figure 6:
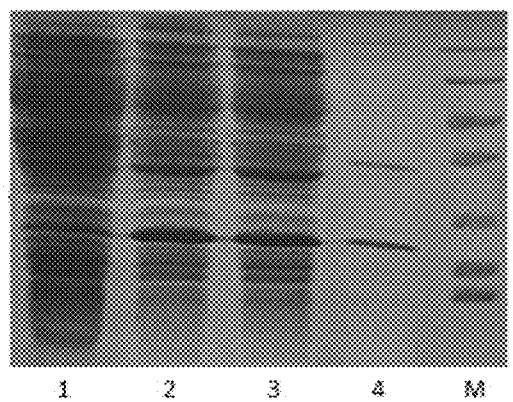
FIG. 6: SDS-PAGE electrophoretogram of pET32a/TRAIL-Mu3 expression; electrophoresis condition: 15% gel, 200V, 35 min; Lane 1: electrophoresis band of pET32a/TRAIL-Mu3 before induction, Lane 2: electrophoresis band of pET32a/TRAIL-Mu3 after induction, Lane 3: electrophoresis band of supernatant of pET32a/TRAIL-Mu3 after bacteria disruption, Lane 4: electrophoresis band of precipitate of pET32a/TRAIL-Mu3 after bacteria disruption, M: Unstained Protein Molecular Weight Marker (molecular weights of bands from top to bottom: 116.0 KDa, 66.2 KDa, 45.0 KDa, 35.0 KDa, 25.0 KDa, 18.4 KDa and 14.4 KDa), loading amount of Marker being 5 μl, and loading amount of other samples being 20 μl.
Figure 7:
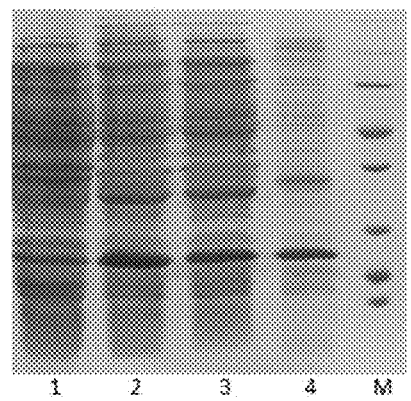
FIG. 7: SDS-PAGE electrophoretogram of pTWIN1/TRAIL-Mu3 expression; electrophoresis condition: 15% gel, 200V, 35 min; Lane 1: electrophoresis band of pTWIN1/TRAIL-Mu3 before induction, Lane 2: electrophoresis band of pTWIN1/TRAIL-Mu3 after induction, Lane 3: electrophoresis band of supernatant of pTWIN1/TRAIL-Mu3 after bacteria disruption, Lane 4: electrophoresis band of precipitate of pTWIN1/TRAIL-Mu3 after bacteria disruption, M: Unstained Protein Molecular Weight Marker (molecular weights of bands from top to bottom: 116.0 KDa, 66.2 KDa, 45.0 KDa, 35.0 KDa, 25.0 KDa, 18.4 KDa and 14.4 KDa), loading amount of Marker being 5 μl, and loading amount of other samples being 20 μl.

For experimental electrophoregrams, see FIG. 6 (pTWIN1/TRAIL-Mu3) and FIG. 7 (pET32a/TRAIL-Mu3), both of which show higher expression, and show that most of expressed products have a higher soluble expression ratio in supernatant after baterial disruption.

Embodiment 5

Purification and Preparation of TRAIL-Mu3 Protein

According to exploration of a large number of lab scale crafts with respect to TRAIL-Mu3, we established a TRAIL-Mu3 protein purification process, and we used a three-step method including SP-HP cation exchange, hydroxyapatite and anion exchange penetrating model for batch purification of TRAIL-Mu protein, to obtain samples for use in activity analysis in vivo and in vitro.

Experimental Procedures

I. Bacteria Disruption and Centrifugation

1. Take 10 g of expressed TRAIL-Mu3 bacteria, add $Na_2CO_3$, glycerol, Tween 20, DTT and NaCl to achieve the final concentrations of above substances of 20 mM, 5%, 0.1%, 1 mM and 500 mM respectively, and in addition, add $H_2O$ to achieve a total volume of 80 ml.

2. Disrupt bacteria by ultrasonic waves, with a bacteria disruption condition: disrupting bacteria with Φ10 probe, 500 W pulse for 2 s, then pausing for 2 s, and disrupting bacteria for 15 min in total.

3. Centrifuge by using a 5430R Model centrifuge and F-35-6-30 Model rotor at 7850 rpm for 40 min, take supernatant, and filter with a 0.45 µm filter membrane for use as a loading sample.

II. Preparation of Purified Protein Solution and Columns

1. Formulate the Following Solutions:

(1) Cation exchange buffer A: 20 mM $Na_2CO_3$—$NaHCO_3$, 0.5M NaCl, 5% glycerol, 0.1% Tween 20 and 1 mM DTT, with pH adjusted to 10.40.

(2) Cation exchange buffer B: 20 mM $Na_2CO_3$—$NaHCO_3$, 1.5M NaCl, 5% glycerol, 0.1% Tween 20 and 1 mM DTT, with pH adjusted to 10.20.

(3) 0.5M NaOH.

(4) 2M NaCl.

(5) Hydroxyapatite pre-equilibration solution: 500 mM $Na_2HPO_4$—$NaH_2PO_4$, with pH adjusted to 7.0.

(6) Hydroxyapatite equilibration solution: 10 mM $Na_2HPO_4$—$NaH_2PO_4$ and 6 ppm $Ca^{2+}$, with pH adjusted to 7.0.

(7) SNS buffer: 25 mM Tris, 25 mM NaCl and 10 mM $Na_2HPO_4$—$NaH_2PO_4$, with pH adjusted to 7.75.

(8) Hydroxyapatite buffer A: 10 mM $Na_2HPO_4$—$NaH_2PO_4$ and 15 ppm $Ca^{2+}$, with pH adjusted to 7.0.

(9) Hydroxyapatite buffer B: 10 mM $Na_2HPO_4$-$NaH_2PO_4$, 15 ppm $Ca^{2+}$ and 1.5M NaCl, with pH adjusted to 7.0.

(10) Anion exchange buffer: 20 mM $Na_2HPO_4$—$NaH_2PO_4$, 0.06M NaCl and 0.3M glycine, with pH adjusted to 7.0.

(11) Diluent: 15 mM $Na_2HPO_4$—$NaH_2PO_4$ and 9 ppm $Ca^{2+}$, with pH adjusted to 4.5.

2. Use an SP Sepharose Fast Flow gel chromatography column, rinse ethanol residual on the column with 5CV pure water, and then equilibrate with 5CV corresponding equilibration buffer.

3. Use an MPC HCT XK16 Grad gel chromatography column, rinse and dilute NaOH on the column with 1CV pure water, then equilibrate with 5CV pre-equilibration buffer, and equilibrate with equilibration buffer.

4. Use a Sephadex G-25 medium gel chromatography column, rinse ethanol residual on the column with 5CV pure water, and then equilibrate with 5CV anion exchange buffer.

5. Use a Q Sepharose Fast Flow gel chromatography column, rinse ethanol residual on the column with 5CV pure water, and then equilibrate with 5CV anion exchange buffer.

III. Purification by Cation Exchange

Purification by cation exchange is performed according to the following purification steps. All penetration and elution components are collected during purification for electrophoretic analysis:

1. Equilibration: Use cation exchange buffer A to equilibrate the SP Sepharose Fast Flow chromatography column until being UV stable.

2. Sample preparation and loading: Take centrifugal supernatant of disrupted bacteria, and load the sample.

3. Washing: Wash the column with 2CV cation exchange buffer A to remove residual unbound protein.

4. Elution: Elute target protein with 3CV cation exchange buffer B.

5. NaOH washing: Wash the column with 2CV 0.5M NaOH solution.

6. Reequilibration: Reequilibrate the column with 5CV cation exchange buffer A.

IV. Purification by Hydroxyapatite

Purification by hydroxyapatite is performed according to the following purification steps. All penetration and elution components are collected during purification for electrophoretic analysis:

1. Equilibration: Use hydroxyapatite equilibration buffer to equilibrate the MPC HCT XK16 Grad chromatography column until being UV stable.

2. Sample preparation and loading: Take a sample of cation exchange eluent, add 2 folds of diluent to dilute into a sample containing 500 mM NaCl, and load the sample.

3. Washing: Wash the column with 2CV hydroxyapatite equilibration buffer to remove residual unbound protein.

4. SNS: Wash the column with 6CV SNS buffer, and control pH.

5. NaCl elution: Equilibrate the column with 2CV hydroxyapatite buffer A, and then elute the target protein with 5CV hydroxyapatite buffer B.

6. Phosphate radical elution: wash the column with 2CV hydroxyapatite pre-equilibration buffer to remove the proteins or impurities which are not eluted by NaCl.

7. Water washing: Wash the column with 0.5CV sterile water to avoid formation of trisodium phosphate precipitate.

8. NaOH washing: Elute the remaining impurities with 5CV 0.5M NaOH solution and store the column.

V. Purification by Anion Exchange

Purification by anion exchange of the third step is performed according to the following purification steps. All penetration and elution components are collected during purification for electrophoretic analysis:

1. Equilibration: Use anion exchange buffer to equilibrate the Q Sepharose Fast Flow chromatography column until being UV stable.

2. Sample preparation and loading: Take a sample of hydroxyapatite purified eluent, exchange the buffer with anion exchange buffer through the Sephadex G-25 medium chromatography column, and then load the sample.

3. Equilibration buffer washing: Wash the column with 1CV anion exchange buffer to obtain the target protein unbound on the column.

4. NaCl washing: Wash the column with 2CV 2M NaCl to remove the protein bound on the column.

5. NaOH washing: Wash the column with 2CV 0.5M NaOH solution.

6. Reequilibration: Reequilibrate the column with anion exchange buffer.

Experimental Results

Figure 8:
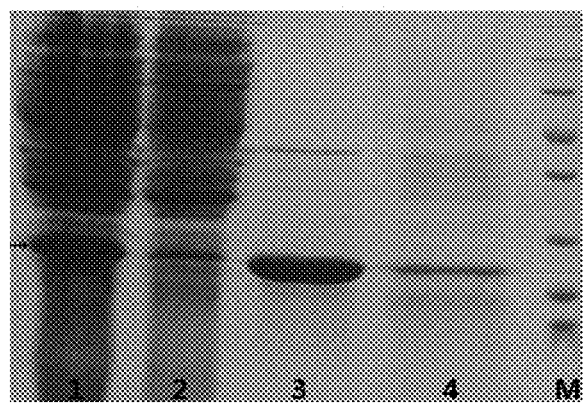
FIG. 8: SDS-PAGE electrophoretogram of the cation exchange process; electrophoresis condition: 15% gel, 200V, 50 min; Lane 1: stock solution for cation exchange; Lane 2: penetrating solution for cation exchange; Lane 3: eluent of cation exchange; Lane 4: NaOH eluent of cation exchange; M: Unstained Protein Molecular Weight Marker (molecular weights of bands from top to bottom: 116.0 KDa, 66.2 KDa, 45.0 KDa, 35.0 KDa, 25.0 KDa, 18.4 KDa and 14.4 KDa); sample loading amount of Marker being 5 μl, and loading amount of others being 20 μl.
Figure 9:
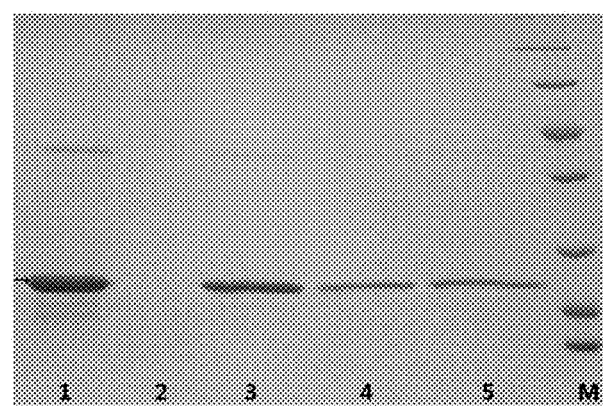
FIG. 9: SDS-PAGE electrophoretogram of the hydroxyapatite process; electrophoresis condition: 15% gel, 200V, 50 min; Lane 1: stock solution for hydroxyapatite loading; Lane 2: penetrating solution of hydroxyapatite; Lane 3: NaCl eluent of hydroxyapatite, Lane 4: phosphate radical eluent of hydroxyapatite, Lane 5: NaOH eluent of hydroxyapatite, M: Unstained Protein Molecular Weight Marker (molecular weights of bands from top to bottom: 116.0 KDa, 66.2 KDa, 45.0 KDa, 35.0 KDa, 25.0 KDa, 18.4 KDa and 14.4 KDa); sample loading amount of Marker being 5 μl, and loading amount of others being 20 μl.
Figure 10:
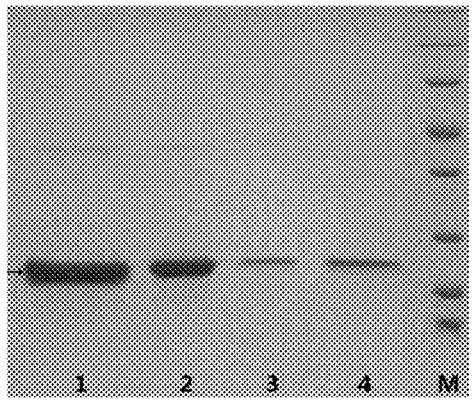
FIG. 10: SDS-PAGE electrophoretogram of the anion exchange process; electrophoresis condition: 15% gel, 200V, 50 min; Lane 1: stock solution for anion exchange; Lane 2: penetrating solution for anion exchange; Lane 3: 2M NaCl eluent; Lane 4: 0.5M NaOH eluent; M: Unstained Protein Molecular Weight Marker (molecular weights of bands from top to bottom: 116.0 KDa, 66.2 KDa, 45.0 KDa, 35.0 KDa, 25.0 KDa, 18.4 KDa and 14.4 KDa); sample loading amount of Marker being 50, and loading amount of others being 20 μl.

For electrophoresis results of the sample in each step of purification, see FIGS. 8, 9 and 10; 15 ml of SP eluent was collected in the first step at a concentration of 2.273 mg/ml, and purity of the target protein was detected to be high already; 12 ml of hydroxyapatite eluent was collected in the second step at a concentration of 2.080 mg/ml, with the effect of removing remaining impurity protein and part of pyrogens, and 20 ml of anion exchange penetrating solution was collected in the third step at a concentration of 0.846 mg/ml, mainly for removing the pyrogens. An amount of protein enough to perform biological activity evaluation was obtained by repeating experiment operations of the Embodiment for multiple times.

Embodiment 6

Western Blot Detection of TRAIL-Mu3 Protein

Because TRAIL-Mu3 is obtained by mutating 5 sites at N-terminal of the wild-type TRAIL, antigenic determinants of TRAIL are still remained, and can specifically bind to a polyclonal antibody of TRAIL, the polyclonal antibody of TRAIL can be used for detection and identification.

Experimental Procedures

I. Sample Preparation

1. TRAIL-Mu3 protein purified in Embodiment 5 is diluted into 1 mg/ml with ultrapure water after being thawed from −20° C. 50 μl of the sample is added to 50 μl 2× loading buffer to prepare electrophoresis sample. 10 μl of each is taken for electrophoresis, namely the loading amount is 5 μg.

2. A control TRAIL-20131204 lyophilized product (prepared in the laboratory) is dissolved with 1 ml PBS, and 50 μl of the sample is added to 50 μl 2× loading buffer to prepared electrophoresis sample. 10 μl of each is taken for electrophoresis, namely the loading amount is 5 μg.

II. Detection Process

The sample is transferred to a PVDF membrane after being separated by 15% SDS-PAGE electrophoresis. First, the sample is blocked at 4° C. overnight, and incubated with a primary antibody [rabbit anti-human TRAIL polyclonal antibody (1:500)] at room temperature for 2 h, then incubated with a secondary antibody [goat anti-rabbit IgG-HRP (1:5000)] at room temperature for 2 h, and finally detected by using enhanced chemiluminescence (ECL). Concrete steps are as follows:

1. Purification of protein by 15% SDS-PAGE electrophoresis: The gel is taken out, and edges of the gel are cut off and soaked in TBST buffer for 15 min.

2. Transfer (wet transfer) by PVDF membrane: PVDF membranes must be slightly wetted with methanol for 15 s, then soaked in distilled water for 1-3 min, and subsequently equilibrated in transfer buffer; spongy cushion, filter papers (4-8 pieces), target gel, PVDF membrane, filter papers (4-8 pieces) and spongy cushion are sequentially spread in a transfer clip from the cathode to the anode, the clip is fastened fixedly after removing bubbles and put into a transfer tank at a voltage of 40V for 45 min.

3. Blocking membrane: The membrane is blocked in blocking solution (3% BSA) under the condition of 4° C. overnight, taken out on the second day and vibrated at room temperature for 30 min, to block nonspecific binding sites.

4. Primary antibody incubation: The primary antibody is diluted with the blocking solution to a working concentration [rabbit anti-human TRAIL polyclonal antibody (1:500)], vibrated together with the membrane and incubated at room temperature for 2 h.

5. Washing membrane: The membrane is washed with TBST for three times, 10 min each. A 10×10 cm membrane needs more than 50 ml of washing solution.

6. Secondary antibody incubation: The secondary antibody labeled with HRP is diluted with the blocking solution to a working concentration [goat anti-rabbit IgG-HRP (1:5000)], vibrated together with the membrane and incubated at room temperature for 2 h.

7. Washing membrane: The membrane is washed with TBST for three times, 10 min each. A 10×10 cm membrane needs more than 50 ml of washing solution.

8. Color development: (1) Solution A and Solution B of equal volume are mixed to prepare enough detection mixture (0.125 ml/cm$^2$). The detection mixture should be used immediately after being prepared and can keep stable at room temperature for 1 h. (2) Excessive washing solution on the washed blotting membrane is removed, but the membrane can not be dried. The detection mixture is added on one side of the membrane with protein, and excessive detection mixture is removed, the membrane is put onto Kodak gel-imaging Image Station 4000R for exposure with X-ray, and the exposure time is first selected to be 1 min and adjusted according to image results. The images are recorded by a computer.

9. Judgement of results: Positive result should present significant color band. Negative result has no color developed.

Experimental Results

Figure 11:
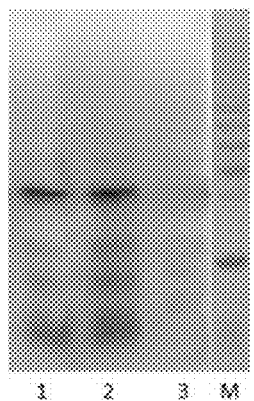
FIG. 11: diagram of Western blot identification results; Lane 1: diagram of western blot of supernatant of pET32a/Mu3-TRAIL after bacteria disruption; Lane 2: diagram of western blot of supernatant of pET32a/TRAIL after bacteria disruption; Lane 3: diagram of western blot of supernatant of BL21(DE3) vacant bacteria after bacteria disruption; M: Thermo Scientific PageRulerPrestained Protein Ladder (molecular weights of bands from top to bottom: 170 Kd, 130 Kd, 100 Kd, 70 Kd, 55 Kd, 40 Kd, 35 Kd, 25 Kd, 15 Kd and 10 Kd)

As shown in FIG. 11, TRAIL-Mu3 and TRAIL control show positive reaction, and the negative control shows negative reaction.

Embodiment 7

Bioactivity Analysis of Protein TRAIL-Mu3 and TRAIL

IC50 values of in vitro antiproliferative activities of 2 protein samples TRAIL-Mu3 and wild-type TRAIL for 32 tumor cell strains are detected by a CCK-8 detection kit, to evaluate their in vitro bioactivities Materials and Methods All cell strains for detection are from Shanghai Cell Bank of Chinese Academy of Sciences or American ATCC.

|   |  | Name of cell strains | Sources of cells |
|---|---|---|---|
| 1 | Pancreatic cancer cell (5) | MIAPaCa-2 | Ordered from American ATCC |
| 2 |  | CFPAC-1 | Ordered from Shanghai Cell Bank of Chinese Academy of Sciences |
| 3 |  | Panc 05.04 | Ordered from American ATCC |
| 4 |  | BxPC-3 | Ordered from Shanghai Cell Bank of Chinese Academy of Sciences |
| 5 |  | PANC-1 | Ordered from Shanghai Cell Bank of Chinese Academy of Sciences |
| 6 | Lung cancer cell (5) | NCI-H460 | Ordered from Shanghai Cell Bank of Chinese Academy of Sciences |
| 7 |  | A 549 | Ordered from Shanghai Cell Bank of Chinese Academy of Sciences |
| 8 |  | NCI-H522 | Ordered from American ATCC |
| 9 |  | H146 | Ordered from American ATCC |
| 10 |  | NCI-H226 | Ordered from American ATCC |
| 11 | Colon (rectal) cancer cell (5) | HCT-15 | Ordered from Shanghai Cell Bank of Chinese Academy of Sciences |
| 12 |  | COLO 205 | Ordered from Shanghai Cell Bank of Chinese Academy of Sciences |
| 13 |  | SW620 | Ordered from Shanghai Cell Bank of Chinese Academy of Sciences |
| 14 |  | HT-29 | Ordered from Shanghai Cell Bank of Chinese Academy of Sciences |
| 15 |  | HCT 116 | Ordered from Shanghai Cell Bank of Chinese Academy of Sciences |
| 16 | Breast cancer cell (5) | MDA-MB-435s | Ordered from American ATCC |
| 17 |  | MDA-MB-231 | Ordered from American ATCC |
| 18 |  | MCF-7 | Ordered from American ATCC |
| 19 |  | T47D | Ordered from American ATCC |
| 20 |  | ZR-75-1 | Ordered from Shanghai Cell Bank of Chinese Academy of Sciences |
| 21 | Myeloid-derived tumor cell (6) | Molt4 | Ordered from American ATCC |
| 22 |  | K562 | Ordered from Shanghai Cell Bank of Chinese Academy of Sciences |
| 23 |  | RPMI8226 | Ordered from American ATCC |
| 24 |  | HL-60 | Ordered from Shanghai Cell Bank of Chinese Academy of Sciences |
| 25 |  | L540cy | Ordered from Shanghai Cell Bank of Chinese Academy of Sciences |
| 26 |  | OPM-2 | Ordered from Shanghai Cell Bank of Chinese Academy of Sciences |
| 27 | Brain tumor cell (3) | U87-MG | Ordered from American ATCC |
| 28 |  | SH-Sy5y-2 | Ordered from American ATCC |
| 29 |  | U251 | Ordered from American ATCC |
| 30 | Osteo-chondroma cell (3) | U-20S | Ordered from American ATCC |
| 31 |  | SaoS-2 | Ordered from American ATCC |
| 32 |  | HT1080 | Ordered from Shanghai Cell Bank of Chinese Academy of Sciences |

Reagents and Consumables
Cell Counting Kit-8 (Cat# CK04-13, Dojindo)
96-well culture plate (Cat#3599, Corning Costar)
Fetal bovine serum (Cat#10099-141, GIBCO)
Culture medium (Purchased from GIBCO)
Desktop microplate reader SpectraMax M5 Microplate Reader (Molecular Devices)
2 protein samples: prepared through Embodiment 5 or in laboratory.

Experimental Procedures
1. Formulation of Reagents
Formulation of Culture Medium

|   |  | Name of cell strains | Culture medium and culture condition | Inoculum density |
|---|---|---|---|---|
| 1 | Pancreatic cancer cell (5) | MIAPaCa-2 | DMEM + 10% FBS + 2.5% horse serum; $CO_2$, 5%; 37.0° C. | $5 \times 10^3$/well |
| 2 |  | CFPAC-1 | IMDM + 10% FBS; $CO_2$, 5%; 37.0° C. | $7 \times 10^3$/well |
| 3 |  | Panc 05.04 | RPMI-1640 + 15% FBS + 10 ug/mL human recombinant insulin + 4.5 g/L glucose; $CO_2$, 5%; 37.0° C. | $4.5 \times 10^3$/well |
| 4 |  | BxPC-3 | RPMI-1640 + 10% FBS + 1 mM sodium pyruvate; $CO_2$, 5%; 37.0° C. | $4 \times 10^3$/well |
| 5 |  | PANC-1 | DMEM + 10% FBS; $CO_2$, 5%; 37.0° C. | $5 \times 10^3$/well |
| 6 | Lung cancer cell (5) | NCI-H460 | RPMI-1640 + 10% FBS; $CO_2$, 5%; 37.0° C. | $8 \times 10^3$/well |
| 7 |  | A 549 | DMEM + 10% FBS; $CO_2$, 5%; 37.0° C. | $5 \times 10^3$/well |
| 8 |  | NCI-H522 | RPMI-1640 + 10% FBS; $CO_2$, 5%; 37.0° C. | $8 \times 10^3$/well |
| 9 |  | H146 | RPMI-1640 + 10% FBS; $CO_2$, 5%; 37.0° C. | $12 \times 10^3$/well |
| 10 |  | NCI-H226 | RPMI-1640 + 10% FBS; $CO_2$, 5%; 37.0° C. | $8 \times 10^3$/well |
| 11 | colon (rectal) cancer cell (5) | HCT-15 | RPMI 1640 + 10% FBS; $CO_2$, 5%; 37.0° C. | $4 \times 10^3$/well |
| 12 |  | COLO 205 | RPMI 1640 + 10% FBS; $CO_2$, 5%; 37.0° C. | $20 \times 10^3$/well |
| 13 |  | SW620 | Leibovitz's L-15 + 10% FBS; without $CO_2$, 37.0° C. | $8 \times 10^3$/well |

-continued

|  |  | Name of cell strains | Culture medium and culture condition | Inoculum density |
|---|---|---|---|---|
|  | 14 | HT-29 | DMEM + 10% FBS; $CO_2$, 5%; 37.0° C. | $5 \times 10^3$/well |
|  | 15 | HCT 116 | DMEM + 10% FBS; $CO_2$, 5%; 37.0° C. | $4 \times 10^3$/well |
| 16 Breast cancer cell (5) |  | MDA-MB-435s | RPMI-1640 + 10% FBS; $CO_2$, 5%; 37.0° C. | $8 \times 10^3$/well |
|  | 17 | MDA-MB-231 | RPMI-1640 + 10% FBS; $CO_2$, 5%; 37.0° C. | $8 \times 10^3$/well |
|  | 18 | MCF-7 | RPMI-1640 + 10% FBS; $CO_2$, 5%; 37.0° C. | $8 \times 10^3$/well |
|  | 19 | T47D | RPMI-1640 + 10% FBS + 0.2 Units/ml bovine insulin; $CO_2$, 5%; 37.0° C. | $10 \times 10^3$/well |
|  | 20 | ZR-75-1 | RPM-1640 + 10% FBS; $CO_2$, 5%; 37.0° C. | $8 \times 10^3$/well |
| 21 Myeloid-derived tumor cell (6) |  | Molt4 | IMDM + 20% FBS; $CO_2$, 5%; 37.0° C. | $13 \times 10^3$/well |
|  | 22 | K562 | RPMI-1640 + 10% FBS + 1 mM sodium pyruvate; $CO_2$, 5%; 37.0° C. | $7 \times 10^3$/well |
|  | 23 | RPMI8226 | MEM + 10% FBS + 1 mM sodium pyruvate; $CO_2$, 5%; 37.0° C. | $6 \times 10^3$/well |
|  | 24 | HL-60 | EMEM + 10% FBS; $CO_2$, 5%; 37.0° C. | $10 \times 10^3$/well |
|  | 25 | L540cy | MEGM + 100 ng/ml cholera toxin; $CO_2$, 5%; 37.0° C. | $6 \times 10^3$/well |
|  | 26 | OPM-2 | DMEM + 10% FBS; $CO_2$, 5%; 37.0° C. | $8 \times 10^3$/well |
| 27 Brain tumor cell (3) |  | U87-MG | IMDM + 20% FBS; $CO_2$, 5%; 37.0° C. | $8 \times 10^3$/well |
|  | 28 | SH-Sy5y-2 | DMEM + 10% FBS; $CO_2$, 5%; 37.0° C. | $8 \times 10^3$/well |
|  | 29 | U251 | EMEM + 10% FBS; $CO_2$, 5%; 37.0° C. | $10 \times 10^3$/well |
| 30 Osteochondroma cell (3) |  | U-20S | IMDM + 20% FBS; $CO_2$, 5%; 37.0° C. | $8 \times 10^3$/well |
|  | 31 | SaoS-2 | RPMI-1640 + 10% FBS + 1 mM sodium pyruvate; $CO_2$, 5%; 37.0° C. | $7 \times 10^3$/well |
|  | 32 | HT1080 | MEM + 10% FBS + 1 mM sodium pyruvate; $CO_2$, 5%; 37.0° C. | $6 \times 10^3$/well |

Preparation of Protein Samples 2 protein samples are diluted with sterile PBS buffer to obtain a final concentration of 5 mg/ml, and filter to remove bacteria.

2. IC50 Test a) Cells in logarithmic growth phase are collected, counted and resuspend cells with complete medium, the cell concentration is adjusted to a suitable concentration (determined according to results of the cell density optimization test), the cells are inoculated onto a 96-well plate, and 100 µl of cell suspension is added to each well. The cells (excluding SW620 cell which does not require 5% $CO_2$) are incubated in a 5% $CO_2$ incubator at 37° C. and 100% relative humidity for 24 h.

b) The protein samples to be tested are diluted to 5 mg/ml with sterile PBS buffer, then gradient diluted for 8 times, and cells are added at 25 µl/well. The compound is gradient diluted 3 folds from 1 mg/ml to 0, with 10 concentration point in total;

c) The cells (excluding SW620 cell which does not require 5% $CO_2$) are incubated in a 5% $CO_2$ incubator at 37° C. and 100% relative humidity for 48 h.

d) The culture medium is drawn and discarded, the complete medium containing 10% CCK-8 is added, and the sample is incubated in an incubator at 37° C. for 2-4 h.

e) The sample is detected on SpectraMax M5 Microplate Reader for absorbance at a wavelength of 450 nm after being gently shaked, and an inhibition ratio is calculated by using the absorbance at 650 nm as a reference.

3. Data Processing

The inhibition ratio of drug for tumor cell growth is calculated according to the following formula: inhibition ratio of tumor cell growth $\% = [(Ac-As)/(Ac-Ab)] \times 100\%$ As: OA/RLU of the sample (cells+CCK-8+compound to be tested)

Ac: OA/RLU of negative control (cells+CCK-8)

Ab: OA/RLU of positive control (medium+CCK-8)

The software Graphpad Prism 5 and the computational formula log (inhibitor) vs. normalized response-Variable slope are used for 1050 curve fitting and calculating IC50 value.

Experimental Results

This experiment tested in vitro cell antiproliferative activities of 2 protein samples (TRAIL-Mu3 and wild-type TRAIL) for 5 pancreatic cancer cell strains (MIAPaCa-2, CFPAC-1, Panc 05.04, BxPC-3 and PANC-1), 5 pulmonary cancer cell strains (NCI-H460, A 549, NCI-H522, H146 and NCI-H226), 5 colon (rectal) cancer cell strains (HCT-15, COLO 205, SW620, HT-29 and HCT 116), 5 breast cancer cell strains (MDA-MB-435s, MDA-MB-231, MCF-7, T47D and ZR-75-1), 6 myeloid-derived tumor cell strains (Molt4, K562, RPMI8226, HL-60, L540cy and OPM-2), 3 brain tumor cell strains (U87-MG, SH-Sy5y-2 and U251) and 3 osteoma and chondroma cell strains (U-20S, SaoS-2 and HT1080). The experimental results are as shown in the table below.

| | Cell type | Cell strains | TRAIL-Mu3 | TRAIL |
|---|---|---|---|---|
| 1 | Pancreatic | MIAPaCa-2 | 0.0004157 | 0.008 |
| 2 | cancer cell (5) | CFPAC-1 | 0.08251 | >100 |
| 3 | | Panc 05.04 | 0.004653 | 0.015 |
| 4 | | BxPC-3 | 0.04881 | >100 |
| 5 | | PANC-1 | 0.00281 | >100 |
| 6 | Lung cancer cell | NCI-H460 | 0.002388 | 0.002 |
| 7 | (5) | A 549 | 4.12 | >100 |
| 8 | | NCI-H522 | 8.156 | >100 |
| 9 | | H146 | 3.002 | >100 |
| 10 | | NCI-H226 | >10 | >100 |
| 11 | Colon (rectal) | HCT-15 | 0.000792 | 0.008 |
| 12 | cancer cell (5) | COLO 205 | 0.002134 | 0.008 |
| 13 | | SW620 | 0.001869 | 0.008762 |
| 14 | | HT-29 | 0.03005 | >100 |
| 15 | | HCT 116 | 0.001543 | 0.015 |
| 16 | Breast cancer | MDA-MB-435s | 0.0005316 | 0.001 |
| 17 | cell | MDA-MB-231 | 0.004246 | 0.003 |
| 18 | (5) | MCF-7 | 0.0006789 | >100 |
| 19 | | T47D | >10 | >100 |
| 20 | | ZR-75-1 | 0.01776 | >100 |
| 21 | Myeloid-derived | Molt4 | 0.001837 | >100 |
| 22 | tumor cell (6) | K562 | 0.01147 | >100 |
| 23 | | RPMI8226 | 0.1512 | >100 |
| 24 | | HL-60 | 0.1174 | 1.465 |
| 25 | | L540cy | 0.4588 | >100 |
| 26 | | OPM-2 | >10 | >100 |
| 27 | Brain tumor cell | U87-MG | >10 | >100 |
| 28 | (3) | SH-Sy5y-2 | >10 | >100 |
| 29 | | U251 | >10 | >100 |
| 30 | Osteochondroma | U-20S | >10 | >100 |
| 31 | cell (3) | SaoS-2 | 0.01985 | >100 |
| 32 | | HT1080 | 0.005441 | 0.02901 |

Comparsion of IC50 values of 32 tumor cell strains (μg/mL)

Experimental Results

Among almost all types of tumor cells which have been detected (including colon (rectal) cancer cell, multiple lung cancer cells, multiple pancreatic cells, multiple breast cancer cells, multiple myeloid-derived tumor cells and multiple osteoma and chondroma cells), compared to the TRAIL wild-type protein, the TRAIL Mutant Membrane-Penetrating Peptide-alike TRAIL-Mu3 has significantly improved antitumor activity, especially for tumor cell strains resistant to the TRAIL wild-type protein, can markedly reverse resistance of these cells to the TRAIL wild-type protein and has greater therapeutic effect.

The above is only better embodiments of the invention, and is not intended to limit the invention, and any modification, equivalent substitution, improvement, etc. made within the spirit and principle of the invention, shall be included within the claimed scope of the invention.

What is claimed is:

1. A TRAIL Mutant Membrane-Penetrating Peptide-alike, wherein the mutant is a protein comprising a Membrane-Penetrating Peptide-alike structure formed by selectively changing an amino acid coding sequence at positions 114-121 of an extracellular fragment of a TRAIL wild-type protein as shown in SEQ ID NO: 5 to a TRAIL mutant protein as shown in SEQ ID NO: 2, namely mutating valine at position 114 into arginine, glutamate at position 116 into arginine, glycine at position 118 into arginine, proline at position 119 into arginine and glutamine at position 120 into arginine, so as to allow the N-terminal of the mutant protein to form an 8-consecutive arginine coding sequence.

2. The TRAIL Mutant Membrane-Penetrating Peptide-alike according to claim 1, wherein the cDNA sequence encoding the said mutant is as SEQ ID NO: 1.

3. A preparation method of the TRAIL Mutant Membrane-Penetrating Peptide-alike according to claim 1, wherein the method comprises the steps as follows:
   A) amplifying and cloning a cDNA fragment as shown in SEQ ID NO: 1;
   B) constructing and identifying an expression vector;
   C) fusing and expressing a recombinant TRAIL protein;
   D) purifying the TRAIL protein; and
   E) identifying the TRAIL protein.

4. The preparation method of the TRAIL Mutant Membrane-Penetrating Peptide-alike according to claim 3, wherein in step B, the step of constructing and identifying the said expression vector comprises:
   $B_1$) excising a fusion tag sequence in a prokaryotic expression vector; and
   $B_2$) cloning an optimized cDNA sequence encoding the TRAIL Mutant Membrane-Penetrating Peptide-alike protein into the prokaryotic expression vector to achieve high-efficiency soluble non-fusion expression.

5. The preparation method of the TRAIL Mutant Membrane-Penetrating Peptide-alike according to claim 4, wherein in step $B_1$, the said prokaryotic expression vector is pET 32a or pTWIN 1.

6. The preparation method of the TRAIL Mutant Membrane-Penetrating Peptide-alike according to claim 3, wherein in step C, when the said recombinant protein is expressed, the induction temperature is 18-24° C.

7. The preparation method of the TRAIL Mutant Membrane-Penetrating Peptide-alike according to claim 3, wherein step D further comprising:
   $D_1$) using cation exchange resin in the first step for purification to capture target a first-time purified TRAIL protein in supernatant after bacteria disruption;
   $D_2$) using hydroxyapatite resin in the second step for moderate purification to further improve purity of the TRAIL protein and remove endotoxin to obtain a second-time purified TRAIL protein; and
   $D_3$) using anion exchange resin in the final step for fine purification to make a third-time purified TRAIL protein to meet requirements for industrialized enlargement and future clinic application.

8. A pharmaceutical compostions comprising the TRAIL Mutant Membrane-Penetrating Peptide-alike according to claim 1.

9. A pharmaceutical compostions comprising the TRAIL Mutant Membrane-Penetrating Peptide-alike according to claim 2.

* * * * *

SEQUENCE LISTING

```
<160> NUMBER OF SEQ ID NOS: 7

<210> SEQ ID NO 1
<211> LENGTH: 513
<212> TYPE: DNA
<213> ORGANISM: Artificial Sequence
<220> FEATURE:
<223> OTHER INFORMATION: cDNA encoding mutant

<400> SEQUENCE: 1
atgcgtcgtc gtcgtcgtcg tcgtcgtgtg gctgctcaca tcactggtac tcgtggtcgt      60
tctaacactc tttcttctcc gaactctaaa aacgaaaaag ctcttggtcg taaaatcaac     120
tcttgggaat cttctcgttc tggtcactct ttcctttcta accttcacct tcgtaacggt     180
gaacttgtta tccacgaaaa aggtttctac tacatctact ctcagactta cttccgtttc     240
caggaagaaa tcaaagaaaa cactaaaaac gataaacaga tggttcagta catctacaaa     300
tacacctctt acccggaccc gatccttctt atgaaatctg ctcgtaactc ttgctggtct     360
aaagatgctg aatacggtct ttactctatc taccagggtg gtatcttcga acttaaagaa     420
aacgatcgta tcttcgtttc tgttactaac gaacacctta tcgatatgga tcacgaggct     480
tctttcttcg gtgctttcct tgttggttaa taa                                   513

<210> SEQ ID NO 2
<211> LENGTH: 281
<212> TYPE: PRT
<213> ORGANISM: Artificial Sequence
<220> FEATURE:
<223> OTHER INFORMATION: amino acid sequence of the mutant
```

<400> SEQUENCE: 2

```
Met Ala Met Met Glu Val Gln Gly Gly Pro Ser Leu Gly Gln Thr Cys
1               5                   10                  15
Val Leu Ile Val Ile Phe Thr Val Leu Leu Gln Ser Leu Cys Val Ala
            20                  25                  30
Val Thr Tyr Val Tyr Phe Thr Asn Glu Leu Lys Gln Met Gln Asp Lys
        35                  40                  45
Tyr Ser Lys Ser Gly Ile Ala Cys Phe Leu Lys Glu Asp Asp Ser Tyr
    50                  55                  60
Trp Asp Pro Asn Asp Glu Glu Ser Met Asn Ser Pro Cys Trp Gln Val
65                  70                  75                  80
Lys Trp Gln Leu Arg Gln Leu Val Arg Lys Met Ile Leu Arg Thr Ser
                85                  90                  95
Glu Glu Thr Ile Ser Thr Val Gln Glu Lys Gln Asn Ile Ser Pro
            100                 105                 110
Leu Arg Arg Arg Arg Arg Arg Arg Val Ala Ala His Ile Thr Gly
        115                 120                 125
Thr Arg Gly Arg Ser Asn Thr Leu Ser Ser Pro Asn Ser Lys Asn Glu
130                 135                 140
Lys Ala Leu Gly Arg Lys Ile Asn Ser Trp Glu Ser Ser Arg Ser Gly
145                 150                 155                 160
His Ser Phe Leu Ser Asn Leu His Leu Arg Asn Gly Glu Leu Val Ile
                165                 170                 175
His Glu Lys Gly Phe Tyr Tyr Ile Tyr Ser Gln Thr Tyr Phe Arg Phe
            180                 185                 190
Gln Glu Glu Ile Lys Glu Asn Thr Lys Asn Asp Lys Gln Met Val Gln
        195                 200                 205
Tyr Ile Tyr Lys Tyr Thr Ser Tyr Pro Asp Pro Ile Leu Leu Met Lys
    210                 215                 220
Ser Ala Arg Asn Ser Cys Trp Ser Lys Asp Ala Glu Tyr Gly Leu Tyr
225                 230                 235                 240
Ser Ile Tyr Gln Gly Gly Ile Phe Glu Leu Lys Glu Asn Asp Arg Ile
                245                 250                 255
Phe Val Ser Val Thr Asn Glu His Leu Ile Asp Met Asp His Glu Ala
            260                 265                 270
Ser Phe Phe Gly Ala Phe Leu Val Gly
        275                 280
```

<210> SEQ ID NO 3
<211> LENGTH: 49
<212> TYPE: DNA
<213> ORGANISM: Artificial Sequence
<220> FEATURE:
<223> OTHER INFORMATION: upstream primer Mu3-TR -NdeI

<400> SEQUENCE: 3
ggtcatatgc gtcgtcgtcg tcgtcgtcgt cgtgtggctg ctcacatca                49

<210> SEQ ID NO 4
<211> LENGTH: 41
<212> TYPE: DNA
<213> ORGANISM: Artificial Sequence
<220> FEATURE:
<223> OTHER INFORMATION: downstream primer TR-Eco-R

<400> SEQUENCE: 4
gttgaattct tattaaccaa caaggaaagc accgaagaaa g                        41

```
<210> SEQ ID NO 5
<211> LENGTH: 281
<212> TYPE: PRT
<213> ORGANISM: Unknown
<220> FEATURE:
<223> OTHER INFORMATION: amino acid sequence of the TRAIL wild-type
      protein

<400> SEQUENCE: 5

Met Ala Met Met Glu Val Gln Gly Gly Pro Ser Leu Gly Gln Thr Cys
1               5                   10                  15

Val Leu Ile Val Ile Phe Thr Val Leu Leu Gln Ser Leu Cys Val Ala
            20                  25                  30

Val Thr Tyr Val Tyr Phe Thr Asn Glu Leu Lys Gln Met Gln Asp Lys
        35                  40                  45

Tyr Ser Lys Ser Gly Ile Ala Cys Phe Leu Lys Glu Asp Asp Ser Tyr
    50                  55                  60

Trp Asp Pro Asn Asp Glu Glu Ser Met Asn Ser Pro Cys Trp Gln Val
65                  70                  75                  80

Lys Trp Gln Leu Arg Gln Leu Val Arg Lys Met Ile Leu Arg Thr Ser
                85                  90                  95

Glu Glu Thr Ile Ser Thr Val Gln Glu Lys Gln Gln Asn Ile Ser Pro
            100                 105                 110

Leu Val Arg Glu Arg Gly Pro Gln Arg Val Ala Ala His Ile Thr Gly
        115                 120                 125

Thr Arg Gly Arg Ser Asn Thr Leu Ser Ser Pro Asn Ser Lys Asn Glu
    130                 135                 140

Lys Ala Leu Gly Arg Lys Ile Asn Ser Trp Glu Ser Ser Arg Ser Gly
145                 150                 155                 160

His Ser Phe Leu Ser Asn Leu His Leu Arg Asn Gly Glu Leu Val Ile
                165                 170                 175

His Glu Lys Gly Phe Tyr Tyr Ile Tyr Ser Gln Thr Tyr Phe Arg Phe
            180                 185                 190

Gln Glu Glu Ile Lys Glu Asn Thr Lys Asn Asp Lys Gln Met Val Gln
        195                 200                 205

Tyr Ile Tyr Lys Tyr Thr Ser Tyr Pro Asp Pro Ile Leu Leu Met Lys
    210                 215                 220

Ser Ala Arg Asn Ser Cys Trp Ser Lys Asp Ala Glu Tyr Gly Leu Tyr
225                 230                 235                 240

Ser Ile Tyr Gln Gly Gly Ile Phe Glu Leu Lys Glu Asn Asp Arg Ile
                245                 250                 255

Phe Val Ser Val Thr Asn Glu His Leu Ile Asp Met Asp His Glu Ala
            260                 265                 270

Ser Phe Phe Gly Ala Phe Leu Val Gly
        275                 280

<210> SEQ ID NO 6
<211> LENGTH: 12
<212> TYPE: PRT
<213> ORGANISM: Artificial Sequence
<220> FEATURE:
<223> OTHER INFORMATION: amino acid sequence of TAT polypetideds

<400> SEQUENCE: 6

Gly Arg Lys Lys Arg Arg Gln Arg Arg Arg Gly Tyr
1               5                   10
```

```
<210> SEQ ID NO 7
<211> LENGTH: 21
<212> TYPE: PRT
<213> ORGANISM: Artificial Sequence
<220> FEATURE:
<223> OTHER INFORMATION: amino acid sequence of PEP-1

<400> SEQUENCE: 7

Lys Glu Thr Trp Trp Glu Thr Trp Trp Thr Glu Trp Ser Gln Pro Lys
1               5                   10                  15

Lys Lys Arg Lys Val
            20
```